US010463855B2

United States Patent
Ruffini et al.

(10) Patent No.: US 10,463,855 B2
(45) Date of Patent: Nov. 5, 2019

(54) METHOD AND A SYSTEM FOR OPTIMIZING THE CONFIGURATION OF MULTISITE TRANSCRANIAL CURRENT STIMULATION AND A COMPUTER-READABLE MEDIUM

(71) Applicants: NEUROELECTRICS BARCELONA S.L., Barcelona (ES); BETH ISRAEL DEACONESS MEDICAL CENTER, Boston, MA (US)

(72) Inventors: Giulio Ruffini, Barcelona (ES); Oscar Ripolles Mateu, Castellon (ES); Alvaro Pascual-Leone, Wayland, MA (US); Michael D. Fox, Newton, MA (US); Pedro Michael Cavaleiro Miranda, Lisbon (PT)

(73) Assignees: NEUROELECTRICS BARCELONA S.L., Barcelona (ES); BETH ISRAEL DEACONESS MEDICAL CENTER, Boston, MA (US)

( * ) Notice: Subject to any disclaimer, the term of this patent is extended or adjusted under 35 U.S.C. 154(b) by 108 days.

(21) Appl. No.: 15/596,555

(22) Filed: May 16, 2017

(65) Prior Publication Data

US 2017/0340882 A1 Nov. 30, 2017

Related U.S. Application Data

(63) Continuation of application No. 14/058,517, filed on Oct. 21, 2013, now Pat. No. 9,694,178.

(51) Int. Cl.
*A61N 1/36* (2006.01)
*A61N 1/04* (2006.01)

(52) U.S. Cl.
CPC ........ *A61N 1/36025* (2013.01); *A61N 1/0456* (2013.01)

(58) Field of Classification Search
CPC .......................... A61N 1/36025; A61N 1/0456
See application file for complete search history.

(56) References Cited

U.S. PATENT DOCUMENTS 8,494,627 B2 7/2013 Bikson et al.
9,089,708 B2 7/2015 Grill et al.
(Continued)

FOREIGN PATENT DOCUMENTS

| CN | 102698360 | 10/2012 |
| WO | 2006138702 | 12/2006 |
| WO | 2010120823 | 10/2010 |

OTHER PUBLICATIONS

Antal et al., "Transcranial alternating current stimulation (tACS)," Frontiers in Human Neuroscience, Jun. 2013, vol. 7, Article 317.
(Continued)

*Primary Examiner* — Catherine M Voorhees
*Assistant Examiner* — Natasha Patel
(74) *Attorney, Agent, or Firm* — Morgan, Lewis & Bockius LLP

(57) ABSTRACT

A system and a method for optimizing the configuration of multisite transcranial current stimulation, including providing an electric field characteristic target map on the brain's cortex, the target map including multiple cortical targets, the multiple cortical targets are localized and/or continuously varying and spatially extended, providing a weight map on the cortical surface prioritizing the important of areas in the target map for the purposes of optimization; and calculating, based on the target and weight maps, optimal currents and optimal locations for a plurality of electrodes intended for providing transcranial current stimulation to globally stimulate at once the multiple cortical targets with excitatory, inhibitory or neutral stimulation.

20 Claims, 4 Drawing Sheets
(4 of 4 Drawing Sheet(s) Filed in Color)

(56) References Cited

U.S. PATENT DOCUMENTS

| | | | |
|---|---|---|---|
| 2005/0060009 A1 | 3/2005 | Goetz | |
| 2010/0152813 A1 | 6/2010 | Lineaweaver et al. | |
| 2011/0288400 A1* | 11/2011 | Russell | A61B 5/055 600/411 |
| 2012/0163689 A1 | 6/2012 | Böttger et al. | |
| 2012/0197105 A1 | 8/2012 | Mezer et al. | |
| 2012/0245653 A1* | 9/2012 | Bikson | A61N 1/36025 607/45 |
| 2012/0265261 A1* | 10/2012 | Bikson | A61N 1/36025 607/2 |
| 2012/0296569 A1* | 11/2012 | Shahaf | A61B 5/048 702/19 |
| 2012/0330622 A1 | 12/2012 | Butson et al. | |
| 2013/0096363 A1 | 4/2013 | Schneider et al. | |
| 2013/0221961 A1 | 8/2013 | Liu | |
| 2014/0350380 A1 | 11/2014 | Eidelberg | |

OTHER PUBLICATIONS

Batsikadze et al., "Partially non-linear stimulation intensity-dependent effects of direct current stimulation on motor cortex excitability in humans," J Physiol 591.7 (2013) pp. 1987-2000.
Bikson et al., "Effects of uniform extracellular DC electric fields on excitability in rat hippocampal slices in vitro," J Physiol 557.1 (2004) pp. 175-190.
Buckner et al., "Opportunities and limitations of intrinsic functional connectivity MRI," Nature Neuroscience, vol. 16, No. 7, Jul. 2013, pp. 832-837.
Chib et al., "Noninvasive remote activation of the ventral midbrain by transcranial direct current stimulation of prefrontal cortex," Citation: Transl Psychiatry (2013) 3.
Day et al., "Electric and Magnetic Stimulation of Human Motor Cortex: Surface EMG and Single Motor Unit Responses," J Physiol (1989), 412, pp. 449-473.
Dayan et al., "Noninvasive brain stimulation: from physiology to network dynamics and back," Nature Neuroscience, vol. 16, No. 7, Jul. 2013, pp. 838-844.
Dmochowski et al., "Targeted transcranial direct current stimulation for rehabilitation after stroke," NeuroImage 75 (2013) 12-19.
Drevets et al., "The Subgenual Anterior Cingulate Cortex in Mood Disorders," CNS Spectr 13:8, Aug. 2008, pp. 663-681.
Ferrucci et al., "Transcranial direct current stimulation in severe, drug-resistant major depression," J. Affective Disorders (2009) 5 pages.
Fonov et al., "Unbiased nonlinear average age-appropriate brain templates from birth to adulthood," NeuroImage, vol. 47, Supplement 1, Jul. 2009, pp. S102.
Fonov et al., "Unbiased Average Age-Appropriate Atlases for Pediatric Studies," NeuroImage, Jan. 1, 2011; 54 (1): 313-327.
Fox Eet al., "The human brain is intrinsically organized into dynamic, anticorrelated functional networks," PNAS, Jul. 5, 2005, vol. 102, No. 27, pp. 9673-9678.
Fox et al., "Clinical applications of resting state functional connectivity," Frontiers in Systems Neuroscience, Jun. 2010, vol. 4, Article 19.
Fox et al., "Measuring and manipulating brain connectivity with resting state functional connectivity magnetic resonance imaging (fcMRI) and transcranial magnetic stimulation (TMS)," NeuroImage, 2012, 12 pages.
Fox et al., "Efficacy of Transcranial Magnetic Stimulation Targets for Depression is Related to Intrinsic Functional Connectivity with the Subgenual Cingulate," Biol. Psychiatry 2012, 9 pages.
Fox et al., "Identification of reproducible individualized targets for treatment of depression with TMS based on intrinsic connectivity," NeuroImage 66 (2013) 151-160.
Fox et al., "Column-Based Model of Electric Field Excitation of Cerebral Cortex," Human Brain Mapping 22:1-16 (2004).
Fregni et al., "Treatment of major depression with transcranial direct current stimulation," Letters to the Editor, Bipolar Disorders 2006:8:203-205.
Frohlich et al., "Endogenous Electric Fields May Guide Neocortical Network Activity," Neuron 67, 129-143, Jul. 15, 2010.
Kammer et al., "Anisotropy in the visual cortex investigated by neuronavigated trnscranial magnetic stimulation," NeuroImage 36 (2007) 313-321.
Lindenberg et al., "Bihemispheric brain stimulation facilities motor recovery in chronic stroke patients," Neuorology 75, Dec. 14, 2010, 2176-2184.
Loo et al., "Transcranial direct current stimulation for depression: 3-week, randomized, sham-controlled trial," The British Journal of Psychiatry (2012) 200, 52059.
Mahmoudi et al., "Transcranial direct current stimulation: electrode montage in stroke," Disability and Rehabilitation, 2011: 33 (15-16): 1383-1388.
Mayberg et al., "Deep Brain Stimulation for Treatment-Resistant Depression," Neuron, vol. 45, 651-660, Mar. 3, 2005.
Merlet et al., "From Oscillatory Transcranial Current Stimulation to Scalp EEG Changes: A Biophysical and Physiological Modeling Study," PLOS ONE, Feb. 2013,vol. 8, Issue 2.
Miranda Eet al., "The electric field in the cortex during transcranial current stimulation," NeuroImage 70 (2013) 48-58.
Molaee-Ardekani et al., "Effects of transcranial Direct Current Stimulation (tDCS) on cortical activity: A computational modeling study," Brain Stimulation 6 (2013) 25-39.
Mukamel et al., "Coupling Between Neuronal Firing, Field Potentials, and fMRI in Human Auditory Cortex," Reports: Science, vol. 309, Aug. 5, 2005, 951-954.
Nitsche et al., "Shaping the Effects of Transcranial Direct Current Stimulation of the Human Motor Cortex," J. Neurophysiol. 97: 3109-3117, Apr. 2007.
Palm et al., "Transcranial direct current stimulation in treatment resistant depression: a randomized double-blind, placebo-controlled study," Brain Stimulation (2001) Articles in Press, 10 pages.
Radman et al., "Role of cortical cell type and morphology in subthreshold and suprathreshold uniform electric field stimulation in vitro," Brain Stimulation (2009) 2, 215-228.e3.
Rahman et al., "Cellular effects of acute direct current stimulation: somatic and synaptic terminal effects," 3. Physiol. 591.10 (2013) 2563-2578.
Ranck, "Which Elements are Excited in Electrical Stimulation of Mammalian Central Nervous System: A Review," Brain Research 98 (1975) 417-440.
Rattay, "Analysis of Models for External Stimulation of Axons," IEEE Transactions on Biomedical Engineering, vol. BME-33, No. 10, Oct. 1986, 974-977.
Ray et al., "Complex networks in brain electrical activity," EPL, 79, Aug. 2007, 38004-p1-38004-p5.
Roth, "Mechanisms for Electrical Stimulation of Excitable Tissue," Critical Reviews in Biomedical Engineering, 22 (3/4):253-305 (1994).
Ruffini et al., "Transcranial Current Brain Stimulation (tCS): Models and Technologies," IEEE Transactions on Neural Systems and Rehabilitation Engineering, vol. 21, No. 3, May 2013, 333-345.
Rushton, "The Effect Upon the Threshold for Nervous Excitation of the Length of Nerve Exposed, and the Angle Between Current and Nerve," J. Physiol. 63, 1927, 357-377.
Sadleir et al., "Target optimization in transcranial direct current stimulation," Frontiers in Psychiatry, Oct. 17, 2012, vol. 3, Article 90.
Shafi et al., "Exploration and Modulation of Brain Network Interactions with Noninvasive Brain Stimulation in Combination with Neuroimaging," Eur 3 Neurosci. Mar. 2012: 35(6): 805-825.
Buzsaki et al., "Neuronal Oscillations in Cortical Networks," Science, vol. 304, Jun. 25, 2004, 1926-1929.
Khedr et al., "Effect of Anodal Versus Cathodal Transcranial Direct Current Stimulation on Stroke Rehabilitation: a Pilot Randomized Controlled Trial," Neurorehabilitation and Neural Repair 27, 592-601.

(56) References Cited

OTHER PUBLICATIONS

Mayberg, "Targeted electrode-based modulation of neural circuits for depression," The Journal of Clinical Investigation, vol. 119, No. 4, Apr. 2009, 717-725.
Paulus, " Transcranial electrical stimulation (tES—TDCS; tRNS, tACS) methods," Neuropsychological Rehabilitation, 2011, 21 (5), 602-617.
Matlab The Language of Technical Computing, http://www.mathworks.com/products/matlab.com.
Mitchell, "An Introduction of Genetic Algorithms," Copyright © 1996 Massachusetts Institute of Technology., 1-158.
Buzsaki, "Rhythms of the Brain," Copyright © 2006 by Oxford University Press, Inc. (465 pages).
International Search Report, International Application No. PCT/IB2014/002180, dated Jan. 1, 2015, 3 pages.

* cited by examiner

METHOD AND A SYSTEM FOR OPTIMIZING THE CONFIGURATION OF MULTISITE TRANSCRANIAL CURRENT STIMULATION AND A COMPUTER-READABLE MEDIUM

FIELD OF THE INVENTION

The present invention generally relates to a method and a system for optimizing the configuration of multisite (i.e., using 2 or more electrodes at different scalp locations) transcranial current stimulation, based on the provision of weighted target maps of the brain's cortex, and the calculation therefrom of optimal currents and optimal locations for a plurality of electrodes intended to globally stimulate at once multiple cortical targets with excitatory, inhibitory or neutral stimulation.

The present invention also relates to a computer-readable medium containing program instructions for a computer to perform a method for optimizing the configuration of multisite transcranial current stimulation.

BACKGROUND OF THE INVENTION

Transcranial current stimulation (tCS) is a noninvasive brain stimulation technique in which weak, constant or slowly varying electrical currents are applied to the brain through the scalp. tCS includes a family of related noninvasive techniques including direct (tDCS), alternating (tACS) and random noise current stimulation (tRNS). These techniques use scalp electrodes with electrode current intensity to area ratios of about 0.3-5 A/m2 at low frequencies (typically <1 kHz) resulting in weak electric fields in the brain, with amplitudes of about 0.2-2V/m. The neuromodulatory effect of these fields
(Antal et al., 2008; Nitsche and Paulus, 2001, 2000; Terney et al., 2008) have been confirmed in many laboratories. In a typical tDCS experiment, a continuous current of 1-2 mA is applied for up to 20 min through two large stimulation electrodes (25-35 cm2). For therapeutic applications, such as post-stroke rehabilitation (Khedr et al. (2013)) or the treatment of depression (Loo et al. (2012)), tDCS is usually applied daily for five days, during one or more weeks.

While tCS interventions typically focus on a single cortical target, it is widely recognized today that many behavioral manifestations of neurological and psychiatric diseases are not solely the result of abnormality in one isolated brain region but represent alterations in brain networks (see, e.g., Fox et al. (2012c) and references therein). In this context, and provided a specification for the location and type of stimulation effects is available, brain networks become the target of neuromodulatory interventions. Advances in neuroimaging technology such as positron emission tomography (PET), electroencephalography (EEG), magnetoencephalography (MEG) and resting-state functional connectivity MRI (rs-fcMRI) are allowing us to non-invasively visualize brain networks in humans with unprecedented clarity. In a parallel and timely development, technologies have become available today which enable the use of more than two electrodes for stimulation (two is the minimum number for current stimulation), making possible true current-controlled multisite stimulation of brain networks. Determining the ideal configuration of a multi-electrode tCS system, however, is complicated by the fact that transcranial brain stimulation effects are largely non-local due to Ohmnic propagation effects. For this reason, optimization algorithms based on globally defined, cortical targeting data are needed.

As an especially interesting example, the use of rs-fcMRI seed maps is herein discussed (Shafi et al. (2012); Fox et al. (2012c)) for defining cortically extended tCS targets. In contrast to traditional task-based fMRI, resting state fcMRI examines correlations in spontaneous fluctuations in the blood oxygen level dependent (BOLD) signal in the absence of any explicit input or output, while subjects simply rest in the scanner (see, e.g., Buckner et al. (2013) and references therein). A consistent observation is that regions with similar functional properties, such as the left and right motor cortices, exhibit coherent BOLD fluctuations even in the absence of movement under resting conditions. Negative correlations (anti-correlations) between regions with apparent opposing functional properties have also been observed (Fox et al. (2005)). Significant rs-fcMRI abnormalities have been identified across almost every major neurological and psychiatric disease (for a review see Fox and Greicius (2010)), and differences across subjects in rs-fcMRI are reproducible across scanning sessions and have been related to individual differences in anatomical connectivity and behavior.

One of the most valuable clinical uses of rs-fcMRI may be to predict how focal brain stimulation will propagate through networks, thus informing the ideal site for stimulation (Fox and Greicius (2010); Fox et al. (2012c)). Recently, Fox et al. (2012b) used rs-fcMRI to identify differences in functional connectivity between effective and less effective DLPFC stimulation sites (Fox et al. (2012c,a)). Significant differences in connectivity were seen with the subgenual cingulate (SG), a region repeatedly implicated in antidepressant response and an effective DBS target (Mayberg et al. (2005); Drevets et al. (2008); Mayberg (2009)). Based on this finding, Fox et al. used rsfcMRI with the SG to identify theoretically optimal TMS target coordinates in the left DLPFC (Fox et al. (2012b)). A similar strategy can be applied to other neurological diseases with effective or potentially effective DBS sites including Parkinson's disease, dystonia, essential tremor, Alzheimer's disease, and even minimally conscious state. An important challenge with this approach is that rs-fcMRI with an effective DBS site does not identify just a single cortical site, but many. In fact, it provides a continuous pattern across the cortical surface of regions that are both positively and negatively correlated with the deep brain stimulation site of interest. Realizing the full potential of this targeting approach thus requires the ability to simultaneously excite or inhibit multiple sites across the surface of the cortex. As will be seen below, the same occurs with targets from other imaging techniques, such as PET. While conventional TMS and tDCS technologies allow for only one or two stimulation sites, the multi-electrode approach perfectly complements this scientific and therapeutic need.

Next, some patent documents disclosing different proposals regarding the optimization of the configuration of multisite transcranial current stimulation are cited and briefly described.

U.S. Pat. No. 8,494,627 B2 discloses the automatic optimization of different parameters for multisite brain stimulation regarding an optimal stimulation pattern (such as voltage, current, activation time, location, sequence or number of electrodes), based on a forward model for the brain tissue obtained using finite element model and taking into account the brain response to different features, such as using a minimum number of electrodes, of current sources, giving a desired orientation of induced electric fields/current density, considering the electrical conductance as non-isotropic and or non-uniform, defining certain constraints such as maximum allowable currents of field intensities at various tissue locations.

Different optimization criteria are disclosed in U.S. Pat. No. 8,494,627 B2 formulated as a convex optimization problem and solved with a least one of linearly constrained Least Squares minimization, weighted Least Squares, Linearly Constrained Minimum Variance, maximum magnitude with a linear-norm constrains, or a convex optimization technique, although the scope of protection granted to said patent is limited to the optimizing of a first array of electrodes, the forming and posterior optimizing of a second array of electrodes from the first array of electrodes, by removing therefrom low current electrodes or electrodes with equal current and opposite polarity.

Although it could be deduced from some portions of the disclosure of U.S. Pat. No. 8,494,627 B2, that a cortical normal solution is sought, only concepts of electric fields radial and tangential to the skull to define a target are used and disclosed in detail therein.

U.S. Pat. No. 8,494,627 B2 discloses injecting current at several transcranial locations in a controlled fashion, i.e. a multisite stimulation, but neither a multitarget stimulation, i.e. the use of multisite stimulation to induce electric fields at cortical locations as determined by the choice of one or more well-delineated (isolated) target locations in the cortex with an associated weighting scheme, nor an extended cortical targeting and stimulation thereof, understood as the use of multisite stimulation to induce electric fields in the entire cortex as specified by a cortical target map together with an associated weight map, are disclosed in detail therein.

Chinese Patent Application Pub. No. CN102698360 also relates to the automatic optimization of stimulation parameters for tDCS, and, with that purpose, particularly discloses using a genetic algorithm taking into account current distribution and spatial distribution and weight coefficients, where the stimulation is a multichannel tDCS provided a plurality of channel electrodes of an electrode array, where each channel electrode has an independent control of the polarity and current strength delivered thereto.

CN102698360 does not either disclose a multitarget stimulation nor an extended cortical targeting, but only a multisite stimulation.

U.S. Patent Application Pub. No. US2013/0096363 describes methods, devices and systems for neuromodulation of deep brain targets using a combination of transcranial magnetic stimulation (TMS) and transcranial direct current (DC) stimulation, where the latter is used only to reduce or eliminate side-effects, such as seizures, when modulating one or more deep brain targets. In the specification of US2013/0096363 is stated that although tDCS has been used in conjunction with TMS, the two techniques have been applied only to cortical brain regions, and also that tDCS effectively only reaches the cortical surface of the brain, and not to elements of the brain which are not in contact with the subdural pool of cerebral spinal fluid, because the spread of electrical current depends upon this energy form passing through highly conductive media, thus not disclosing any indirect deep brain stimulation (DBS) to be provided with the tDCS.

US2013/0096363 does not describe either a multitarget stimulation nor an extended cortical targeting.

REFERENCES

Antal, A., Paulus, W., 2013. Transcranial alternating current stimulation (tacs). Frontiers in Human Neuroscience 7, 1-4.

Batsikadze, G., Moliadze, V., Paulus, W., Kuo, M., Nitsche, M., 2013. Partially non-linear stimulation intensity-dependent effects of direct current stimulation on motor cortex excitability in humans. J Physiol 591, 1987-2000.

Bikson, M., Inoue, M., Akiyama, H., Deans, J. K., Fox, J. E., Miyakawa, H., Jefferys, J. G., 2004. Effects of uniform extracellular dc electric fields on excitability in rat hippocampal slices in vitro. J Physiol 557, 175-90.

Buckner, R. L., Krienen, F. M., Yeo, B. T. T., 2013. Opportunities and limitations of intrinsic functional connectivity mri. Nature Neuroscience 16, 832-837.

Buzsaki, G., 2006. Rhythms of the Brain. Oxford University Press Press. Buzsaki, G., Draguhn, A., 2004. Neuronal oscillations in cortical networks. Science 304, 926-19293.

Chib, V. S., Yun, K., Takahashi, H., Shimojo, S., 2013. Noninvasive remote activation of the ventral midbrain by transcranial direct current stimulation of prefrontal cortex. Translational Psychiatry 3.

Day, B., Dressler, D., Maertens de Noordhout, A., Marsden, C., Nakashima, K., Rothwell, J., Thompson, P., 1989. Electric and magnetic stimulation of human motor cortex: surface emg and single motor unit responses. J. Physiol 122, 449-473.

Dayan, E., Censor, N., Buch, E., Sandrini, M., Cohen, L., 2013. Noninvasive brain stimulation: from physiology to network dynamics and back. Nature Neuroscience 16, 638-644.

Dmochowski, J. P., Datta, A., Bikson, M., Su, Y., Parra, L. C., 2011. Optimized multi-electrode stimulation increases focality and intensity at target. Journal of Neural Engineering 8.

Drevets, W., Savitz, J., Trimble, M., 2008. The subgenual anterior cingulate cortex in mood disorders. CNS Spectr 13, 663-81.

Ferrucci, R., Bortolomasi, M., Vergari, M., Tadini, L., Salvoro, B., Giacopuzzi, M., Barbieri, S., Priori, A., 2009. Transcranial direct current stimulation in severe, drug-resistant major depression. J Affect Disord 118, 215-219.

Fonov, V., Evans, A., McKinstry, R., Almli, C., Collins, D., 2009. Unbiased nonlinear average age-appropriate brain templates from birth to adulthood. NeuroImage 47, S102.

Fox, M., Greicius, M., 2010. Clinical applications of resting state functional connectivity. Front Syst Neurosci 4, 19.

Fox, M., Liu, H., Pascual-Leone, A., 2012a. Identification of reproducible individualized targets for treatment of depression with TMS based on intrinsic connectivity. NeuroImage 66C.

Fox, M. D., Buckner, R. L., White, M. P., Greicius, M. D., Pascual-Leone, A., 2012b. Efficacy of transcranial magnetic stimulation targets for depression is related to intrinsic functional connectivity with the subgenual cingulate. Biol Psychiatry 72.

Fox, M. D., Halko, M. A., Eldaief, M. C., Pascual-Leone, A., 2012c. Measuring and manipulating brain connectivity with resting state functional connectivity magnetic resonance imaging (fcMRI) and transcranial magnetic stimulation (TMS). Neuroimage 62, 2232-43.

Fox, M. D., Snyder, A. Z., Vincent, J. L., Corbetta, M., Essen, D. C. V., Raichle, M. E., 2005. The human brain is intrinsically organized into dynamic, anticorrelated functional networks. Proc Natl Acad Sci USA 102, 9673-9678.

Fox, P. T., Narayana, S., Tandon, N., Sandoval, H., Fox, S. P., Kochunov, P., Lancaster, J. L., 2004. Column-based model of electric field excitation of cerebral cortex. Hum Brain Mapp 22, 1-14.

Fregni, F., Boggio, P. S., Nitsche, M. A., Marcolin, M. A., Rigonatti, S. P., Pascual-Leone, A., 2006. Treatment of major depression with transcranial direct current stimulation. Bipolar Disord 8, 203-4.

Fröhlich, F., McCormick, D. A., 2010. Endogenous electric fields may guide neocortical network activity. Neuron 67, 129-143.

Kammer, T., Vorwerg, M., Herrnberger, B., 2007. Anisotropy in the visual cortex investigated by neuronavigated transcranial magnetic stimulation. Neuroimage 36, 313-321.

Khedr, E., Shawky, O., El-Hammady, D., Rothwell, J., Darwish, E., Mostafa, O., Tohamy, A., 2013. Effect of anodal versus cathodal transcranial direct current stimulation on stroke rehabilitation: A pilot randomized controlled trial. Neurorehabil Neural Repair 27, 592-601.

Lindenberg, R., Renga, V., Zhu, L., D, N., G, S., 2010. Bihemispheric brain stimulation facilitates motor recovery in chronic stroke patients. Neurology 75, 2176-84.

Loo, C. K. dand Alonzo, A., Martin, D., Mitchell, P., Galvez, V., Sachdev, P., 2012. Transcranial direct current stimulation for depression: 3-week, randomised, sham-controlled trial. Br J Psychiatry 200, 52-59.

Mahmoudi, H., Haghighi, A. B., Petramfar, P., Jahanshahi, S., Salehi, Z., Fregni, F., 2011. Transcranial direct current stimulation: electrode montage in stroke. Disability and Rehabilitation 33, 1383-1388.

MATLAB, 2009. version 7.9.0 (R2009b). The MathWorks Inc., Natick, Mass.

Mayberg, H., 2009. Targeted electrode-based modulation of neural circuits for depression. J Clin Invest 119, 717-25.

Mayberg, H. S., Lozano, A. M., Voon, V., McNeely, H. E., Seminowicz, D., Hamani, C., Schwalb, J. M., Kennedy, S. H., 2005. Deep brain stimulation for treatment-resistant depression. Neuron 45, 651-660.

Merlet, I., Birot, G., Salvador, R., Molaee-Ardekani, B., Mekkonen, A., Soria-Frish, A., Ruffini, G., Miranda, P., F., W., 2013. From oscillatory transcranial current stimulation to scalp eeg changes: a biophysical and physiological modeling study. PLoS One 8.

Miranda, P. C., Mekonnen, A., Salvador, R., Ruffini, G., 2013. The electricfield in the cortex during transcranial current stimulation. Neuroimage 70, 45-58.

Mitchell, M., 1998. An Introduction to Genetic Algorithms (Complex Adaptive Systems). The MIT Press.

Molaee-Ardekani, B., Márquez-Ruiz, J., Merlet, I., Leal-Campanario, R., c, A. G., Sánchez-Campusano, R., Birot, G., Ruffini, G., Delgado-Garcia, J. M., Wendling, F., 2013. Effects of transcranial direct current stimulation (tDCS) on cortical activity: A computational modeling study. Brain Stimulation 6, 25-39.

Mukamel, R., Gelbard, H., Arieli, A., Hasson, U., Fried, I., Malach, R., 2005. Coupling between neuronal firing, field potentials, and fmri in human auditory cortex. Science 309.

Nitsche, M. A., et al., 2007. Shaping the effects of transcranial direct current stimulation of the human motor cortex. J. Neurophysiol 97, 3109-3117.

Palm, U., Schiller, C., Fintescu, Z., Obermeier, M., Keeser, D and Reisinger, E., Pogarell, O., Nitsche, M., Möller, H., Padberg, F., 2012. Transcranial direct current stimulation in treatment resistant depression: a randomized double-blind, placebo-controlled study. Brain Stimulation 5, 242-51.

Paulus, W., 2011. Transcranial electrical stimulation (tES—tDCS; tRNS, tACS) methods. Neurophysiological Rehabilitation 21, 602-617.

Radman, T., Ramos, R. L., Brumberg, J. C., Bikson, M., 2009. Role of cortical cell type and morphology in subthreshold and suprathreshold uniform electric field stimulation in vitro. Brain Stimulation 2, 28.

Rahman, A., Reato, D., Arlotti, M., Gasca, F., Datta, A., Parra, L. C., Bikson, M., 2013. Cellular effects of acute direct current stimulation: somatic and synaptic terminal effects. J Physiol 591, 2563-2578.

Ranck, J., 1975. Which elements are excited in electrical stimulation of the mammalian central nervous system: a review. Brain Res 98, 417-440.

Rattay, F., 1986. Analysis of models for external stimulation of axons. IEEE Transactions on Biomedical Engineering 33, 974-977.

Ray, C., Ruffini, G., Marco-Pallarés, J., Fuentemilla, L., Grau, C., 2007. Complex networks in brain electrical activity. Europhysics Letters 79.

Roth, B. J., 1994. Mechanisms for electrical stimulation of excitable tissue. Crit Rev Biomed Eng 22, 253-305.

Ruffini, G., Wendling, F., Merlet, I., Molaee-Ardekani, B., Mekkonen, A., Salvador, R., Soria-Frisch, A., Grau, C., Dunne, S., Miranda, P., 2013. Transcranial current brain stimulation (tCS):models and technologies. IEEE Transactions on Neural Systems and Rehabilitation Engineering 21, 333-345.

Rushton, W. A. H., 1927. The effect upon the threshold for nervous excitation of the length of nerve exposed, and the angle between current and nerve. J Physiol 63, 357-77.

Sadleir, R. J., Vannorsdall, T. D., Schretlen, D. J., Gordon, B., 2012. Target optimization in transcranial direct current stimulation. Front Psychiatry 3.

Shafi, M., Westover, M., Fox, M., A, P. L., 2012. Exploration and modulation of brain network interactions with non-invasive brain stimulation in combination with neuroimaging. Eur J Neurosci. 35, 805-25.

DESCRIPTION OF THE INVENTION

It is an object of the present invention to offer an alternative to the prior state of the art, with the purpose of providing a method and a system which, contrary to the known methods and systems, really allows the optimal simultaneous stimulation of multiple cortical targets.

To that end, the present invention relates, in a first aspect, to a method for optimizing the configuration of multisite transcranial current stimulation, comprising:
  providing a possibly signed (positive or negative) target map of electric field characteristics on the brain's cortex, said target map including multiple cortical targets, where said multiple cortical targets are localized (i.e. well-delineated isolated target locations in the cortex) and/or continuously varying and spatially extended;
  providing a weight map on the cortical surface prioritizing the important of areas in said target map for the purposes of optimization; and
  calculating, based on said target and weight maps, optimal currents and optimal locations for a plurality of electrodes intended for providing transcranial current stimulation to globally stimulate at once said multiple cortical targets with excitatory, inhibitory or neutral stimulation, i.e., in order to provide the above mentioned multitarget localized and/or extended cortical stimulation.

For an embodiment, said multiple cortical targets are final targets.

For another embodiment of the method of the present invention, said multiple cortical targets are intermediary targets whose spatially extension patterns indirectly affect, via neuronal interaction, cortical or deeper targets in the brain.

The method comprises, for an embodiment, performing said calculation of optimal currents and electrode locations based on said spatially extension patterns and to their positive or negative correlation with a deep brain stimulation target.

Although an optimization based on cortical surface target maps could be seen as a limitation, in fact it isn't due to the rather large scale of tCS currents compared to grey matter thickness. However, if deeper structures are sought, i.e. for said embodiment where the final target is a deep brain stimulation target, a volume optimization problem can be defined additionally.

According to an embodiment, said spatially extension patterns are specific to a pathology and/or to a patient, hence the method of the present invention provides a transcranial stimulation personalized to said specific pathology and/or to said patient.

The above mentioned target and weight maps are obtained, according to different embodiments, from brain data obtained by means of a brain monitoring technology, such as fMRI, rs-fcMRI, PET, EEG and MEG, or a combination thereof.

Preferably, the calculation of optimal currents and optimal electrode locations is performed based on an optimization of several electric field components as described by the target map, including electric field distribution and orientation, and more preferably the target map includes the definition of targets based on a coordinate system relative to the cortical surface, with targets for at least normal components of respective electric field vectors.

Conventionally, components of electric field vectors of transcranial brain stimulation taken into consideration are radial or normal to the skull (see Dmochowski et al. (2011)), unlike to what is proposed by the method of the present invention were, as stated above, components which are normal to the cortical surface, i.e. to the cortex, are taken into account, both for generating the target map and also for the posterior stimulation of the mapped targets with such components normal to the cortex.

For a more elaborated embodiment, said target map further includes targets for tangential components, to the cortical surface, of respective electric field vectors, or more generally, of the full electric vector field.

According to an embodiment, said calculation of optimal currents and optimal electrode locations is performed under constraints regarding at least maximal electrodes number and maximal current at each electrode and the total current injected into the brain by all electrodes at any time.

The method comprises, for an embodiment, using a realistic head model and electric field modeling to perform said optimization of several electric field components, such as a multilayer finite element model of a realistic head, generic or specific to a patient, where said electric field distribution and orientation is relative to the grey matter and white matter surfaces.

In order to increase focality for a cortical target, according to an embodiment, the above mentioned calculation of optimal currents and electrodes optimal locations generates zero or near zero electric field values for those electrodes surrounding said cortical target of increased focality—as described by the target and weight maps.

Said plurality of electrodes are in a number above two and preferentially above seven, and, for an embodiment, the plurality of electrodes are arranged according to an arbitrary EEG 10-20 or 10-10 or similar montage scheme with determined electrode positions, based on a set of pre-defined locations.

According to an embodiment, the method comprises using constrained least squares to optimize current intensities and a genetic algorithm to optimize electrode number and electrode locations.

Said transcranial stimulation is at least one or a combination of transcranial direct current stimulation, transcranial alternating current stimulation, transcranial random noise stimulation or stimulation with a more generic current waveform.

The present invention also relates, in a second aspect, to a system for optimizing the configuration of multisite transcranial current stimulation, comprising data processing means for:
  providing a target map on the brain's cortex, said target map including multiple cortical targets, where said multiple cortical targets are localized and/or continuously varying and spatially extended;
  providing a weight map on the cortical surface prioritizing the areas in said target map for the purposes of optimization; and
  calculating, based on said target and weight maps, optimal currents and optimal locations for a plurality of electrodes intended for providing transcranial current stimulation to globally stimulate at once said multiple cortical targets, or, more generally, extended cortical patterns, with excitatory, inhibitory or neutral stimulation.

The system of the second aspect of the present invention is adapted to implement the method of the first aspect of the invention.

The present invention also relates, in a third aspect, to a computer-readable medium (preferably non-transitory) containing program instructions for a computer to perform the method for optimizing the configuration of multisite transcranial current stimulation of the first aspect of the invention.

The mechanisms underlying the after-effects of tDCS are still the subject of investigation, but in all cases these local changes are brought about by the accumulated action of the applied electric field over time, directly or indirectly. For this reason, as explained above, the present invention is focused on electric field optimization. Moreover, given that that there are strong directional effects in the interaction of electric fields and neurons, i.e., neurons are influenced mostly by the component of the electric field parallel to their trajectory (Ranck (1975); Rattay (1986); Rushton (1927); Roth (1994); Bikson et al. (2004); Fröhlich and McCormick (2010)), and that the effects of tDCS depend on its polarity, knowledge about the orientation of the electric field is crucial in predicting the effects of stimulation. The components of the field perpendicular and parallel to the cortical surface are of special importance, since pyramidal cells are mostly aligned perpendicular to the surface, while many cortical interneurons and axonal projections of pyramidal cells tend to align tangentially (Day et al. (1989); Fox et al. (2004); Kammer et al. (2007)). Thus, an important element in modeling is to provide the electric field distribution and orientation relative to the grey matter (GM) and white matter (WM) surfaces (the latter might be important to study the possibility of polarizing corticospinal axons, their collaterals and other projection neurons). In order to do this, as stated above, for an embodiment, a realistic head model derived from structural MRI images (Miranda et al. (2013)) to calculate the tCS electric field components rapidly from, for example, arbitrary EEG 10-20 montages is used in both, the method and the system of the present invention. Importantly, this modeling approach allows for fast calculation of electric field components normal and parallel to the GM and WM surfaces.

The method and system of the present invention are intended for optimizing the configuration of multisite transcranial current stimulation of general, spatially extended cortical targets and, as will be shown in a posterior section, how, based on fMRI, PET, EEG or other data specifying target and weight maps on the cortical surface for excitatory, inhibitory or neutral stimulation and a constraint of the maximal number of electrodes, a solution can be produced with the optimal currents and locations of the electrodes. The main features of the present invention, for different embodiments thereof, are:

a) the overall concept of working with extended, weighted cortical pattern target maps based on fMRI, PET, EEG, MEG or other data, b) the emphasis on optimization of one or more electric field components as opposed to its magnitude or intensity, c) the definition of targets based on a coordinate system relative to the cortical surface, with targets for normal and tangential components of electric field, and d) the use of advanced algorithms to optimize not only currents but also the number and location of electrodes given appropriate constraints.

For direct current tCS (tDCS) applications, some examples of implementation of this technique using an available tCS system providing up to 8 small Ag/AgCl stimulation electrodes are provided in a posterior section, where a demonstration of the implementation of the method both for localized and spatially extended targets defined using rs-fcMRI and PET data is given, with clinical applications in stroke and depression.

BRIEF DESCRIPTION OF THE DRAWINGS

The patent or application file contains at least one drawing executed in color. Copies of this patent or patent application publication with the color drawing(s) will be provided by the Office upon request and payment of the necessary fee.

The previous and other advantages and features will be better understood from the following detailed description of embodiments, with reference to the attached drawings, which must be considered in an illustrative and non-limiting manner, in which.

DETAILED DESCRIPTION OF SEVERAL EMBODIMENTS

Figure 1:
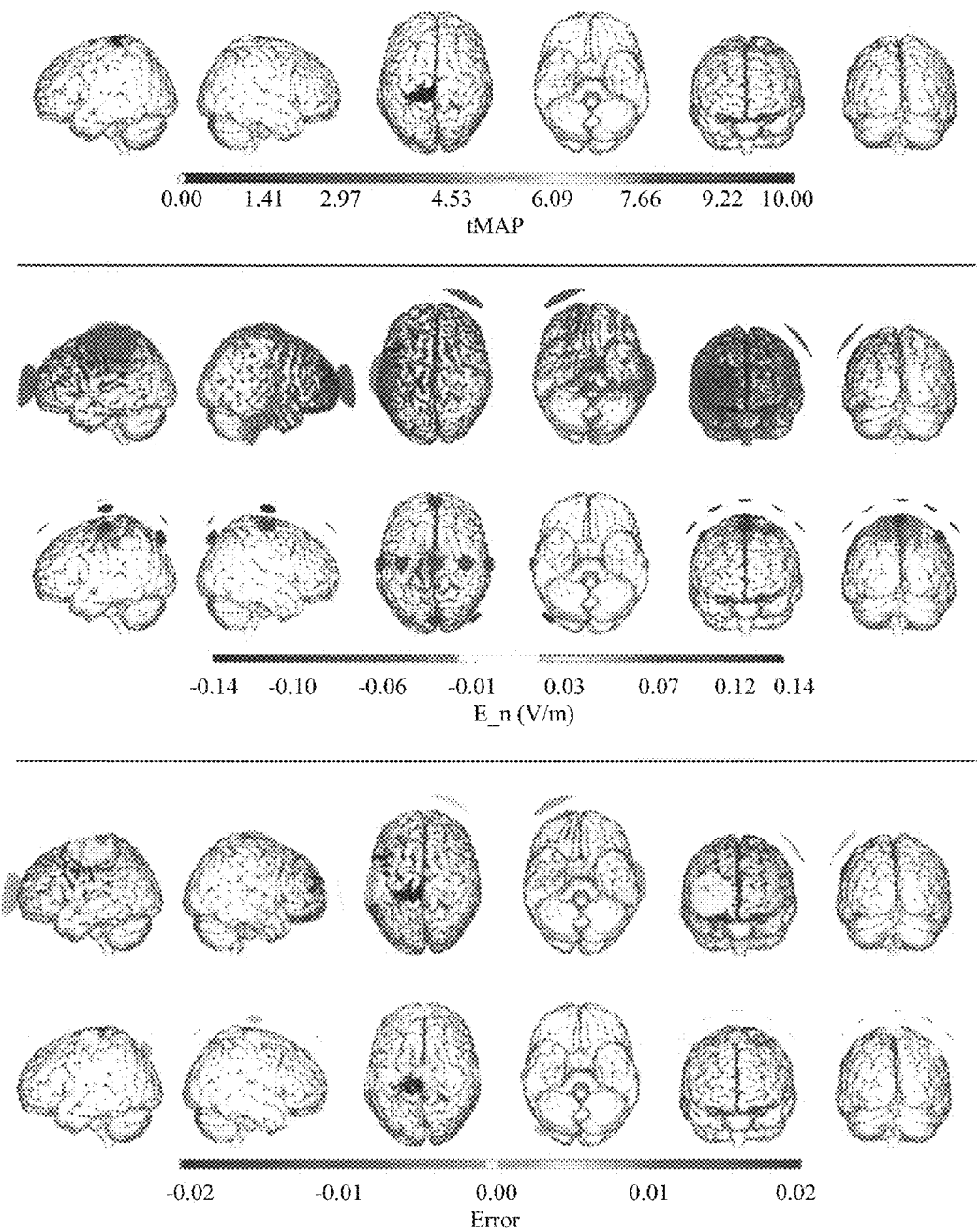
FIG. 1: Montages for unilateral stroke treatment over the left motor cortex. Note the more centralized, "quasi-monopolar" nature of the electric field impact area provided by the 8-electrode solution. First row: target map. The color scale indicates the target value. Red areas are associated to negative electric field (cortical normal component) targets, while blue areas are associated to positive electric field (cortical normal component) targets. Second and third rows: cortical normal electric field maps for a traditional (bipolar, where the two electrodes are depicted as big blue and red circles, respectively) 1 mA montage vs. the 8-electrode (small blue and red circles) optimized solution (1 mA max, 4 mA total max) respectively. The color scale (from blue to red) refers to the amplitude of the normal electric field at the cortical surface. Positive (red) values denote an inward directed cortical normal component of the electric field (in V/m). Fourth and Fifth rows: Weighted Error maps (Err(x) in Equation 1 below) for traditional and 8-electrode solutions respectively. Here, negative values (blue) indicate a better fit than no intervention, positive values (red) a worse fit.

In the present section it is shown how to use neuroimaging data to specify a target map on the cortical surface for excitatory, inhibitory or neutral stimulation, and how, given constraints on the maximal number of electrodes and currents, a solution can be produced with the optimal electrode currents and their, locations. The main differences of the present invention with other recent efforts stem from a) the overall concept of working with extended, weighted cortical pattern target maps based on fMRI, PET, EEG, MEG or other data, b) the emphasis on optimization of an electric field component as opposed to its magnitude or intensity (as in, e.g., Sadleir et al. (2012)), c) the definition of targets based on a coordinate system relative to the cortical surface, with targets for normal $E^\perp$ and tangential $E^\parallel$ components of electric field (as opposed to "radial or normal to the skull" as in Dmochowski et al. (2011)), and d) the use of advanced algorithms to optimize not only currents but also the number and location of electrodes given appropriate constraints. Finally, at the end of this section the generalization of these methods to tACS is addressed, although in a more exploratory fashion.

Methods:

General Statement of the Problem:

The non-invasive stimulation problem can be loosely classified as follows: a) single, isolated, localized target, b) bipolar or, more generally, multi-polar isolated/localized targets and c) cortical pattern targeting. With the single target case an issue that typically arises is how to deal with the return current, since the laws of physics require current conservation and thus a minimum of two electrodes need to be applied. The return (or "reference") electrode is normally positioned in an area which is presumed not to play a role (e.g., "over the contralateral orbit"), and sometimes it is chosen to have a larger area than the "active" one so that its effects diffuse (Nitsche and et al. (2007)). More modern approaches include the so-called "high-definition tDCS", where a return arrangement of electrodes is placed close to the active electrode (see, e.g., Dmochowski et al. (2011) and references therein) or more general quasi-monopolar montages such as the one described below, which employ an array of optimally-placed return electrodes (see below in this section the description of the part referred as "Targeting localized cortical regions" and FIG. 1).

In bipolar or multi-polar targeting, two or more discrete targets are actually sought, some excitatory (anodal) and others inhibitory (cathodal) (as in, e.g., Ferrucci et al. (2009); Lindenberg et al. (2010); Mahmoudi et al. (2011); Chib et al. (2013)). This situation will normally require the use of small electrodes, as electric field defocusing may be an issue if large electrodes are used. An example is provided below (see below "Targeting localized cortical regions" and FIG. 2).

More generally, the possibility of global cortical targeting has been designed to achieve a more effective neuromodulatory outcome. In the case of tDCS, such a map may just be a specification of the areas to excite, inhibit, or leave unaffected, with a particular weighting map for each of them. Examples on the use of PET and rs-fcMRI generated target maps are provided below (see "Cortical pattern target from PET" and "Cortical pattern target from rs-fcMRI", respectively).

In the following, and without loss of generality, the discussion is made concrete by adopting the StarStim device specifications (Neuroelectrics Barcelona, Spain). This device provides up to 8 independently current-controlled stimulation electrodes (allowing for programmable linear combinations of DC, AC or RNS currents at each electrode). The maximal current at any electrode is 2 mA, while for safety the system constraints the maximal current injected into the brain by all electrodes at any time to 4 mA.

Stimulation electrodes (Ag/AgCl "Pi" electrodes, Neuroelectrics Barcelona, Barcelona, Spain) have a radius of 1 cm and provide, through a gel interface, a contact area of $\pi$ cm$^2$. The electrodes can be placed on a cap using an extension of the 10-20 system providing 27 default locations.

Realistic Head Model and Electric Field Modeling:

The electric field calculations described in the present section were performed using the realistic head model described in Miranda et al. (2013). Briefly, tissue boundaries were derived from MR images (scalp, skull, cerebrospinal fluid (CSF) including ventricles, Grey Matter and White Matter) and the Finite Element Method was used to calculate the electric potential in the head, subject to the appropriate boundary conditions. Tissues were assumed to be uniform and isotropic and values for their electric conductivity were taken from the literature.

In order to compute electric fields rapidly, use of the principle of superposition has been made. This states that with appropriate boundary conditions, the solution to a general N-electrode problem can be expressed as a linear combination of N-1 bipolar ones. A fixed reference electrode is first chosen, and then all the bipolar solutions using this electrode are computed. A general solution with an arbitrary number of N electrodes can then easily be computed as follows. The currents to be set can be described by an Nary array of the form $[I_1, \ldots, I_N]$, with the current conservation constraint $I_N = -\Sigma_{n=1}^{N-1} I_n$. Let $E_n$ be the electric field solution for a bipolar setup with currents $[0 \ldots +1 \ldots -1]$ (in some chosen units, with the "+1" in the nth position). For the general multi-electrode case, the electric field due to currents $[I_1 \ldots I_N]$ is simply given by $E = I_1 E_1 + \ldots + I_{N-1} E_{N-1}$.

In the present case, 27 Pi-electrodes were placed on the scalp at the positions available in the standard StarStim cap. The electrodes were represented by cylindrical gel disks with a diameter of 1.0 cm and a height of approximately 2.5 mm. Twenty six different calculations were performed, with the anode always at Cz and the cathode at one of the other 26 positions in the cap, with the current set to 1 mA. The electric field for each one of these bipolar montages was obtained as minus the gradient of the electric potential. The total electric field for a given combination of bipolar montages is computed as the weighted vector sum of the electric field due to each montage. A comparison of such superimposed solutions with the direct calculation showed that the errors involved were completely negligible ($<10^{-8}$ V/m). The electric field distributions associated to traditional electrode montages with two 25 cm$^2$ circular sponge electrodes were also computed in order to compare their performance to the optimized solutions.

In the convention used below, a positive value for the component of the electric field normal to the cortical surface $E^\perp$ means the electric field component normal is pointing into the cortex. As is discussed below, such a field would be excitatory. On the other hand, an electric field pointing out of the cortex (negative normal component) would be inhibitory.

Optimization Problem and Algorithms:

The basic mechanism for neuronal interaction in tCS is presently thought to arise from the coupling of electric fields to populations of elongated neurons such as pyramidal cells (Roth (1994); Bikson et al. (2004); Radman et al. (2009); Rahman et al. (2013); Molaee-Ardekani et al. (2013); Ruffini et al. (2013) and references therein). Non-coincidentally, such populations are also recognized to be the main generators of EEG signals, in a process of spatially coherent oscillation at certain frequencies (see, e.g., Merlet et al.

(2013) and references within). The role of other types of neurons (e.g., interneurons such as basket cells) or other brain cells such as glia is not well understood, since their distribution and connections are complex, but they are in principle less sensitive to such fields due to their more isotropic structures and distributions. Nevertheless, according to this model, a necessary first step in modeling the effects of tCS is to determine the spatial distribution of the generated electric fields in the brain.

At the single neuron level, the external electric field vector forces the displacement of intracellular ions (which mobilize to cancel the intracellular field), altering the neuronal ionic distribution and modifying the transmembrane potential difference. For an ideal straight finite fiber with space constant I and length L» l in a locally homogeneous electric field $\vec{E}$, the transmembrane potential difference is largest at the fiber termination, with a value that can be approximated by $I\vec{E}\cdot\hat{n}$, where $\hat{n}$ is the unit vector parallel to the ideal main fiber axis (see Ranck (1975); Ruffini et al. (2013); Rahman et al. (2013) and references therein). This is essentially a first-order Taylor approximation in the electric field, with a spatial scale provided by the membrane space constant", and geometric directions by field and fibre orientation. For short neurons of length L<l, the spatial scale factor tends to L. Thus, longer neurons with a higher membrane space constant will undergo a larger change in membrane potential.

Ideally, in order to define a montage optimization strategy it would be necessary to define the full target vectorial electric field (i.e., all 3 components) values in the cortex or other areas. With such a specification an optimization problem could easily be defined. However, this does not seem possible today. As proxies, desired target values for the magnitude or some of the components of the electric field can be defined. Working with magnitudes is a priori problematic, because the magnitude of the electric field vector or any of its components is invariant under overall current reversal, and there is abundant evidence showing that, in general, current direction is an important parameter in tDCS. Indeed, pyramidal neuron populations in the cortical outer layer display a preferred alignment direction normal to the cortical surface. For this reason, they offer a clear target and preferred direction for tCS stimulation. While other electric field components may no doubt be important (Rahman et al. (2013)), it does not seem presently possible to determine how to specify these components in any polarity sensitive optimization strategy, given the apparent isotropy of connections in directions other than the normal. For these reasons, and without loss of generality, it has been chosen to focus here on the optimization of the component of the electric field normal to the cortical surfaces.

With the fast electric field calculation algorithm in place, the optimization problem is essentially defined by i) a target map on the cortical surface specifying the desired values for the electric field at each point, ii) a weight map providing the degree of relative importance of each location in the target map and, iii) a set of constraints on the number of electrodes and their currents, as described below in "Targeting localized cortical regions".

The Target and Target Weight Maps

The target map can be a user-defined area or areas in the cortical surface. Target maps can be defined ad-hoc by the user, or they can stem from, e.g., fMRI, PET, MEG or EEG data, as described above ("General statement of the problem"). In the latter case techniques such as bandpass filtering and cortical mapping (a simpler version of EEG tomography where the generating dipoles are constrained on the cortical surface) could be used to generate target maps (see the discussion below). Indeed, EEG connectivity analysis can be carried out at the voxel or node level as opposed to electrode space (see, e.g., Ray et al. (2007)), providing a connectivity map similar to that in fcMRI.

The use of rs-fcMRI seed correlation t-test or statistical significance maps (called here "t-maps") is particularly appealing, as it can provide links to deep regions not easily accessible by non-invasive stimulation techniques. However, seed maps can also be used to target cortical locations and networks. Such applications may be of interest for pathologies such as stroke or epilepsy, with seeds defined by cortical lesions. In this way, stimulation may not only directly target the affected region, but the entire cortex exploiting network phenomena.

The algorithm described here as an example of the above considerations starts from the provision of a ternary choice: a given area may be stimulated for excitatory, inhibitory or neutral effects. Such choices basically define the targeted electric field normal component at each region. An electric field target value $E_0^\perp(x)$ can be defined by the user. Here a value based on the tCS literature (Miranda et al. (2013)) has been used, where currents of the order of 1-2 mA are used. For example, $E_0^\perp=+0.3$ V/m is a reasonable target for excitation (electric field direction is defined to be positive here if directed normal and inwards at the cortical surface), $E_0^\perp=-0.3$ V/m for inhibition, and $E_0^\perp=0$ V/m for a neutral effect. The weights assigned to each location typically vary from 0 to 100, biasing the solutions towards some specific targets areas. Such a target map is just an example, since many other possibilities exist.

Current Intensity Optimization

Assuming that a set of electrode locations has been specified, we describe here the process of current intensity optimization given target and weight maps. The generic system of equations to solve for a hypothetical N-electrode system is (for simplicity the ⊥ symbol used to indicate the normal component has been dropped) $[E_1(x) \ldots E_{N-1}(x)] \cdot I = E_0(x)$, where $E_n(x)$ is a basis function solution for a particular bipolar combination (specifying the normal component of the E field at each point x in the mesh), I the array of sought-for currents, and $E_0(x)$ is the target value related to the t-map.

In the case of a statistical t-map target $T(x)$ obtained from, e.g., rs-fcMRI, moreover, a request is made that the equation associated to each mesh point x be weighted by a weight $W(x)$. If the statistical significance t-map magnitude is large at a given cortical location, it is asked that the corresponding equation be enforced strongly, since the location under scrutiny is proportionally statistically significant. This can be implemented by multiplying each row in the target equation above by $W(x)=|T(x)|$. In addition, if the target map at a given location is not statistically significant it may be desired that the solution to have no effect on it, that is, the target electric field for a given lower threshold $T_{min}$ should be set to 0. A minimum weight $W_{min}$ should be set for such cases (e.g., $W(x)=W_{min}=2$). The t-test magnitude chosen as lower threshold will depend on other statistical aspects such as the number of subjects used in the creation of t-test map from rs-fcMRI data.

The optimization problem is formalized using weighted least squares. Mathematically, the goal is to minimize the mean weighted error $x (i)=\Sigma_x Err(x; I)$, where the error at each mesh point x is defined here by (Equation 1)

$$Err(x; I) = \frac{(Y_\omega(x) - E_\omega(x)I)^2 - (Y_\omega(x))^2}{\left(\frac{1}{N_x}\right)\Sigma_x W(x)^2} \quad (1)$$

Here, I are the currents, $N_x$ the number of mesh points and $Y_\omega(x)=E_0 \, T(x)$ if $|T(x)|>T_{min}$, else $Y_\omega(x)=0$, and $E_\omega(x)=E(x)W(x)$. Optimization is subject to the constraints $|I_n|<I_{max}$ for $n=1, \ldots, N$ (with $I_N=-\Sigma_{n=1}^{N-1}I_n$), where $I_{max}$ is the maximal allowed current at any electrode, and $\Sigma_{I_n>0} I_n = (\frac{1}{2}) \Sigma_N |I_N| < I_{max}^T$, where $I_{max}^T$ is the maximal allowed total injected current into the brain.

Genetic Algorithm

Since in general it will be wished for practical reasons to limit the number of electrodes used, a search in the space of electrode locations needs to be carried out. Genetic algorithms (GAs) are often used to solve directed search problems—as is the case here. Briefly, GAs imitate nature by treating candidate solutions to an optimization problem as individuals endowed with a chromosome subject to evolution and natural selection (for an introduction see, e.g., Mitchell (1998)). The genetic algorithm implemented here is, in short, based on the definition of a solution by a "DNA" binary string (in this case of dimension N-1) specifying the electrodes to be used, and uses as optimization function the least squares error, i.e., the one with the best possible current configuration for the chosen electrode locations. Cross-over and mutation functions are defined to ensure that the offspring of solutions do not violate the constraint of maximal number of electrodes in the solution. Once a DNA string is specified (i.e., a particular montage), its fitness is easily computed by inverting the solution for that particular montage. Solutions with more than the maximal number of electrodes desired are penalized strongly. The algorithm, implemented with specifically designed fitness, cross-over and mutation functions, converges rather quickly (in a few hours) and reliably to a solution.

The overall quality of the solution I is quantified by the mean weighted error x (I) (note that x=0 when all currents are set to zero). Another goodness-of-fit measure is provided by the related weighted cross correlation coefficient of target map and electric field, $$cc = \frac{\Sigma_x Y_\omega(x) E_\omega(x) \cdot I}{\sqrt{\Sigma_x (Y_\omega(x))^2 \Sigma_x (E_\omega(x) \cdot I)^2}} \quad (2)$$

a number between −1 and 1. In order to visually assess solution quality as a quality map over the cortical surface, the error Err(x; I) can be used (as in the appended Figures).

EXAMPLES

Next some solutions using the above described technique are provided. In Table 1 a summary of the characteristics of each montage is provided, including a "full-cap" 27 channel solution. It can be observed that increasing the number of electrodes beyond 8 improves the performance of the solution only marginally for these particular target maps, especially the simpler ones.

TABLE 1

Montage comparisons for the four target maps discussed in the present section. Weighted Correlation Coefficient (WCC), mean weighted error $\chi$(I) (mV2/m2), maximal current at any electrode and total injected current (µA) are provided for traditional (bipolar), 8 and 27 channel solutions.

| Target | Montage | WCC | $\chi$(I) | Max I | Tot Inj I |
|---|---|---|---|---|---|
| BA4 Left | Traditional | 0.02 | 163 | 1,000 | 1,000 |
| | 8 Channel | 0.31 | −8 | 1,000 | 1,297 |
| | 27 Channel | 0.31 | −9 | 1,000 | 2,146 |
| BA4 Bilateral | Traditional | −0.07 | 184 | 1,000 | 1,000 |
| | 8 Channel | 0.26 | −13 | 823 | 1,513 |
| | 27 Channel | 0.26 | −14 | 854 | 2,045 |
| rs-fcMRI SG seed map | Traditional | 0.11 | 1 | 1,000 | 1,000 |
| | 8 Channel | 0.29 | −214 | 1,000 | 3,262 |
| | 27 Channel | 0.31 | −239 | 1,000 | 4,000 |
| PET DBS map | Traditional | −0.05 | 125 | 1,000 | 1,000 |
| | 8 Channel | 0.21 | −51 | 843 | 2,236 |
| | 27 Channel | 0.23 | −59 | 1,000 | 4,000 |

Figure 2:
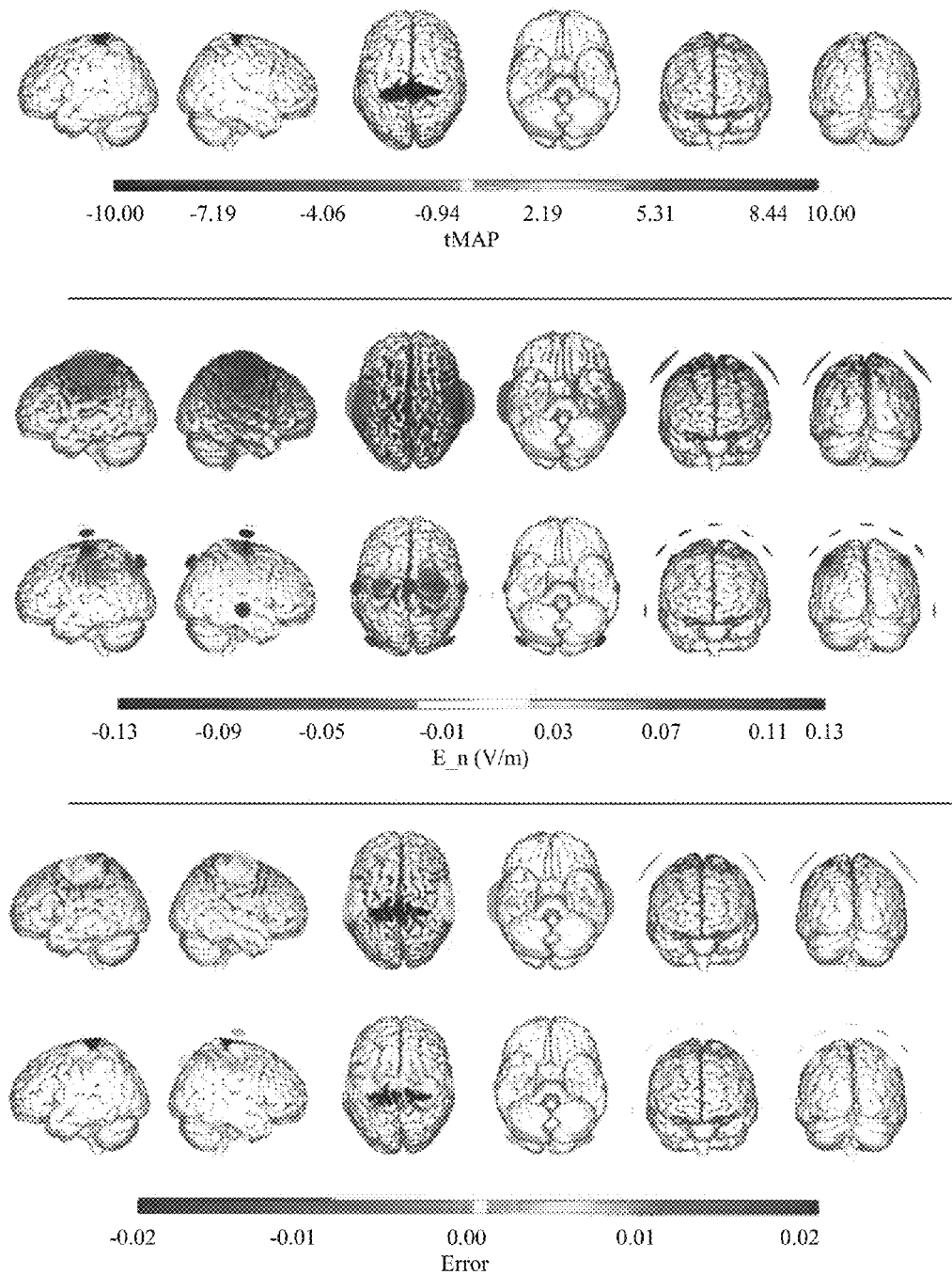
FIG. 2: Montages for bilateral stroke treatment. Note the more centralized nature of the electric field impact area with the multi-electrode solution. First row: target map over the motor cortex on both hemispheres. The color scale indicates the target value. Red areas are associated to negative electric field (cortical normal component) targets, while blue areas are associated to positive electric field (cortical normal component) targets. Second and third rows: cortical normal electric field maps for a traditional (bipolar) 1 mA montage vs. the 8-electrode optimized solution (1 mA max, 4 mA total max) respectively. The color scale (from blue to red) refers to the amplitude of the normal electric field at the cortical surface. Positive (red) values denote an inward directed cortical normal component of the electric field (in V/m). Fourth and Fifth rows: Weighted Error maps (Err(x) in Equation 1 below) for traditional and 8-electrode solutions respectively. Here, negative values (blue) indicate a better fit than no intervention, positive values (red) a worse fit.

Targeting Localized Cortical Regions:

As discussed above, in a typical tDCS study two electrodes are placed on the scalp to target a specific brain region. The effect of the chosen montage depends on the spatial distribution of the vectorial electric field induced in the grey matter (GM) and white matter (WM), and since in a bipolar montage the second electrode will carry the same amount of current as the primary electrode, undesired side effects may occur on the "return" or "reference" site. Consider for example targeting the left motor cortex for excitation, a common approach in stroke rehabilitation (Mahmoudi et al. (2011)). Here the weights for the weight map in the motor cortex areas are chosen to be twice as large as in the rest of the cortex, where the field target is zero. In FIG. 1 a simulation of the electric field using a traditional montage with 25 sq-cm sponges over C3 and FP2 (the contralateral orbit) is provided. The widespread nature of the induced fields can be observed, and the resulting high error as compared to the GA optimized 8 electrode montage (see Table 1 above). It can be noted that weighted cross-correlation coefficients remain relatively low even for the best solutions, reflecting the limited freedom available to adapt to the required weighted target maps. Similarly, FIG. 2 illustrates a bipolar target map used in stroke rehabilitation (e.g., Lindenberg et al. (2010); Mahmoudi et al. (2011)), with one excitatory target on the left motor cortex, the other (inhibitory) on the right. Again, the multi-electrode solution provides a superior fit, with better account for neutral effect target areas.

Figure 3:
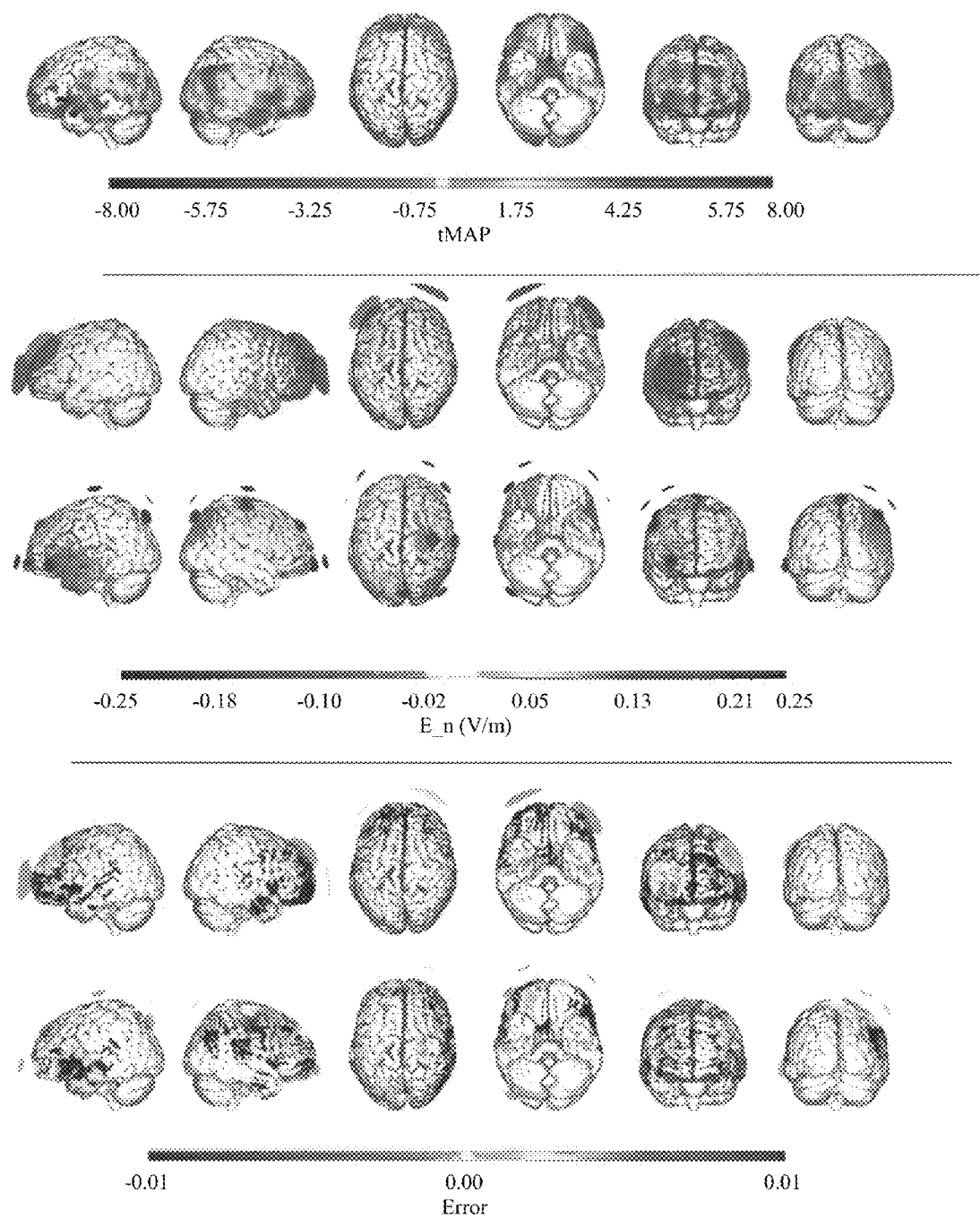
FIG. 3: Montages for depression (from PET data). First row: target map from PET changes in response to DBS therapy for depression. The color scale indicates the target value. Red areas are associated to negative electric field (cortical normal component) targets, while blue areas are associated to positive electric field (cortical normal component) targets. Second and third rows: cortical normal electric field maps for a traditional (bipolar) 1 mA montage vs. the 8-electrode optimized solution (1 mA max, 4 mA total max) respectively. The color scale (from blue to red) refers to the amplitude of the normal electric field at the cortical surface. Positive (red) values denote an inward directed cortical normal component of the electric field (in V/m). Fourth and Fifth rows: Weighted Error maps (Err(x) in Equation 1 below) for traditional and 8-electrode solutions respectively. Here, negative values (blue) indicate a better fit than no intervention, positive values (red) a worse fit.

Cortical Pattern Target from PET:

In FIG. 3 the solution for a cortical target map based on PET data (Mayberg et al. (2005)) is provided. The target reflects cerebral blood flow (CBF) changes in response to deep brain stimulation therapy for treatment resistant major depression. Accordingly, the optimization problem is designed (target map) to excite regions where CBF has increased, and inhibit regions where CBF decreases, with target weights for the weight map proportional to CBF change magnitude. As can be seen in Table 1, the multisite solution provides a better weighted error and correlation coefficient (Table 1) since it is able to "hit" the target map at several locations, while the classical montage performs rather poorly.

Figure 4:
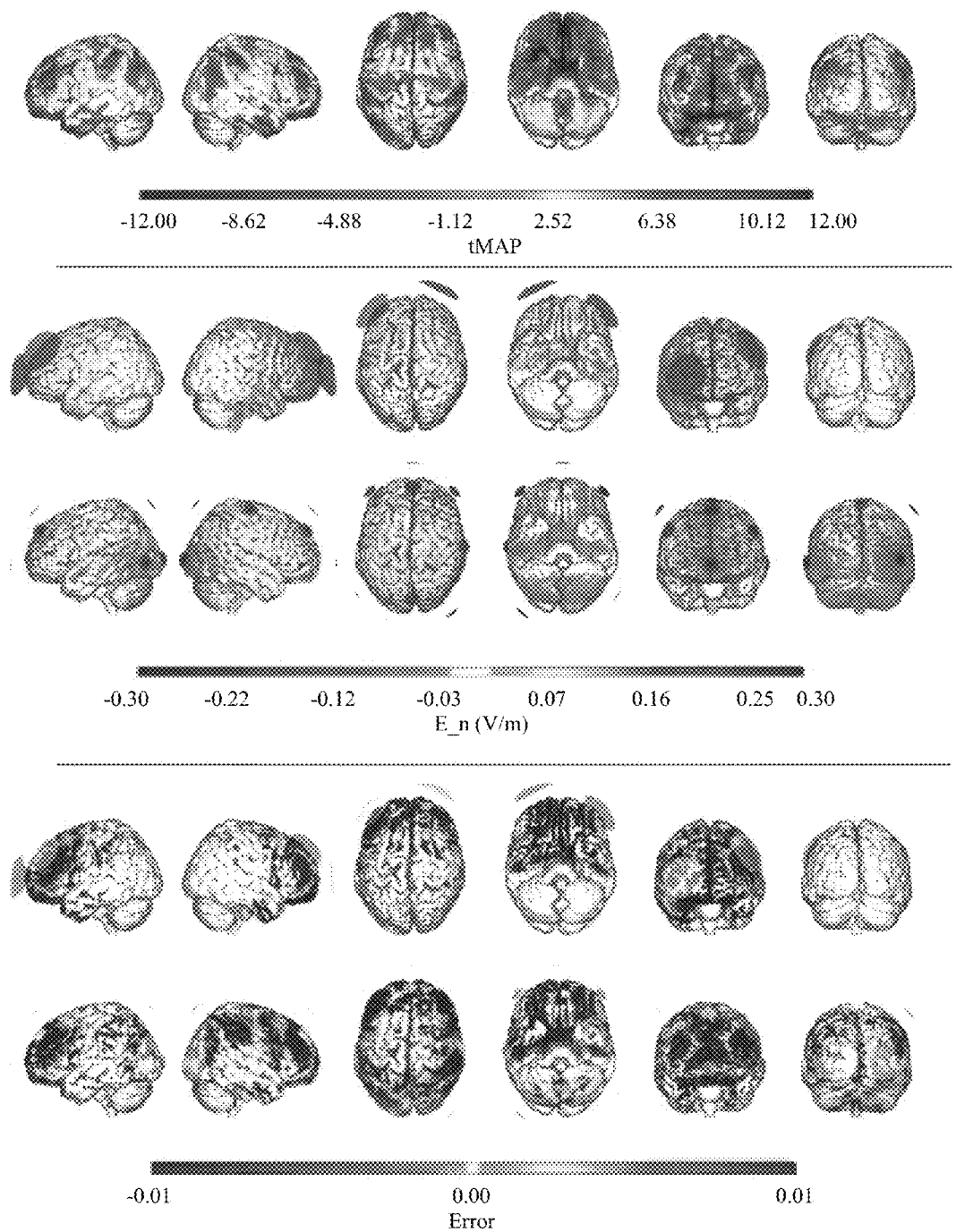
FIG. 4: Montages for depression (from SG rs-fcMRI seed target map). First row: target map. The color scale indicates the target value. Red areas are associated to negative electric field (cortical normal component) targets, while blue areas are associated to positive electric field (cortical normal component) targets. Second and third rows: normal electric field maps for a traditional (bipolar) 1 mA montage vs. the 8-electrode optimized solution (1 mA max, 4 mA total max) respectively. The color scale (from blue to red) refers to the amplitude of the normal electric field at the cortical surface. Positive (red) values denote an inward directed cortical normal component of the electric field (in V/m). Fourth and Fifth rows: Weighted Error maps (Err(x) in Equation 1 below) for traditional and 8-electrode solutions respectively. Here, negative values (blue) indicate a better fit than no intervention, positive values (red) a worse fit.

Cortical Pattern Target from Rs-fcMRI:

Continuing with the example of treatment of resistant major depression, an electrode montage that will excite and inhibit different areas of cortex based on the cortical rsfcMRI correlation statistical t-map pattern with the subgenual cingulate (SG) has been generated, with target weights proportional to t-map magnitude. In this case, the rs-fcMRI t-map needs to be sign reversed to produce the target map, since the goal is inhibition of the associated seed. By exciting anti-correlated areas and inhibiting correlated areas, the present inventors would hypothesize that this stimulation will propagate to and maximally inhibit the SG, improving antidepressant response. Note that on the basis of this target map there is no obvious rationale for using a traditional montage with anodal stimulation over the left dorsolateral prefrontal cortex (DLPFC)—e.g., the rs-fcMRI target map is fairly symmetric. In FIG. 4 the solution to this problem using an 8 electrode montage as opposed to one using a traditional montage is provided, where we target the left DLPFC as depicted by the left Brodmann area BA46 (F3) with a return over Fp2 (see, e.g., Palm et al. (2012); Fregni et al. (2006)). Again, the multi-electrode solution yields a lower weighted error and higher correlation coefficient than the classical montage (Table 1).

Discussion:

The present invention provides a new method and new system for optimization of tDCS montages with extended targets based on realistic head modeling of the components of the electric field as defined by cortical surfaces, which have been described above both from a more conceptual view and from a more particular view (in this section). The advantage of working with the electric field on the cortical surface is that is allows for optimization of the cortical surface normal (or perpendicular) component of the electric field, or of its tangential component, or, e.g., overall magnitude. The methodology is based on current knowledge of the primary interaction of tCS electric fields and the cortex. The optimization problem is defined in terms of a target map which attributes weights to the different mesh points. This concept makes the method of the present invention very flexible and allows for working with one or a few extended uniform targets with simple or arbitrary shapes or, more importantly, with extended targets weighted by some measure of interest such as "activation" or "connectivity" obtained using various imaging modalities, with the ability of specifying the number of electrodes available for stimulation. As an example, focality is achieved by prescribing zero field values at the nodes outside the target for which specific weights can also be specified. Safety in protocol optimization is addressed by limiting the current through each electrode and the total current injected into the brain.

Target maps can be defined from various sources. These include fMRI, EEG—which raises the interesting possibility of closed-loop montage optimization where EEG or fMRI data is used in real time to adjust stimulation parameters—positron emission tomograpy (PET) and near-infrared spectroscopy (NIRS) (Shafi et al. (2012)). These brain imaging methods can be leveraged to provide information both for clinical or research applications. Magnetic resonance spectroscopy (MRS) can provide another potential means to gather additional, relevant neurochemical information that may help define whether excitatory or inhibitory stimulation should be applied to a given node. Diffusion tensor imaging (DTI) data could be used to refine electric field models to take into consideration conductivity anisotropy and also for defining vectorial (oriented) target maps beyond the cortical normal model. Furthermore, methods for aggregating information from these techniques may provide unique, yet insufficiently explored ways to further refine cortical target maps. Future efforts in this area would be valuable.

Even though the realistic simulation of electric fields in the brain is based on solid physics, there is uncertainty on the precise conductivity values to be used. These limitations and others (including the use of isotropic conductivity) in the realistic head modeling used here are discussed in Miranda et al. (2013). Research is on-going on the sensitivity of electric fields to variability of conductivity variables. There is, nevertheless, a high need to contrast these models with measurements, certainly a topic for further work.

It is noted that the model used in the present section is based on the single-subject template Colin27. Other approaches can be envisioned, such as the use of the MNI-152 average model (Fonov et al. (2009)) or, even better, the use of personalized models based on individual scans, which will certainly be necessary in specific cases (e.g., the case of damaged brains or skulls). It is also noted that in the examples above we have used rs-fcMRI group data to define cortical maps. Target maps may eventually require individualization (e.g., individual differences in rs-fcMRI associated to depression have been reported (Fox et al. (2012a)). However, while individualization in either case may add more precision, it is presently unclear in which cases the extra modeling effort will be warranted, given that tCS fields are rather spatially spread. On the other hand, the normal component of the electric field peaks mainly in the bottom of the sulci, and the main sulci are not too variable among different subjects even though their position in the brain can vary by a few centimeters. Similarly, the fact that targets are generally distributed and large (the target maps usually display low spatial frequencies) also means that the electric field is in effect "averaged over" the anatomy, making small anatomical details less relevant.

Finally, it is noted that the basic interaction model used in the embodiments described in the present section, where the effects of stimulation are linearly depending on the electric vector field, may not be accurate in all situations. In order to improve the obtained results for said situations having said not so accurate stimulation effects, non-linear effects in electric field or dosage are taken into account for building and using a more complex and complete model, as it is known that they could play a role (e.g., the direction of the excitability change has recently been shown to be intensity dependent (Batsikadze et al. (2013)).

Clinical research should explore this methodology in selected interesting applications to test its range of validity, with pilot tests in e.g., depression, Parkison's disease or stroke. Comparison of effects using traditional versus multifocal montages in healthy subjects would provide an interesting starting point for such research.

Generalization to tACS:

The generalization of the proposed method to the case of tACS is nontrivial, even though the process for calculation of electric fields for low frequencies (<1 kHz) is essentially the same as for tDCS (the same applies to low frequency tRNS). That is, if $E(x)$ is electric field the solution to a DC current for a particular montage and currents, then $E(x, t)=E(x) \cos(2\pi t f)$ is the solution to the analogous AC case in which each current is multiplied by $\cos(2\pi t f)$. The real difficulty here lies in the choice of a physiological meaningful optimization problem.

Current studies show that support of brain activity involves the orchestrated oscillatory activity of different and spatially separated brain regions (see, e.g., Buzsaki and Draguhn (2004); Buzsaki (2006)). Indeed, a major challenge for neuroscience today is to map and analyze the spatio-temporal patterns of activity of the large neuronal populations that are believed to be responsible for information processing in the human brain. Phase or amplitude synchronization may relate different functional regions operating at the same or different frequencies via cross-frequency synchrony. In principle, tACS is potentially capable of acting on such natural rhythms in brain networks through the process of resonance (Fröhlich and McCormick (2010); Paulus (2011); Ruffini et al. (2013); Dayan et al. (2013); Antal and Paulus (2013)) and devices such as StarStim already allow for the simultaneous multisite stimulation of different cortical regions with specific frequencies and relative phases.

In order to configure properly a multisite monochromatic tACS montage (i.e., one using a single tACS frequency), EEG or MEG data can be used to define the target frequency as well as a target cortical map. The latter could be obtained, e.g., using EEG tomography or cortical mapping algorithms with EEG data filtered at the appropriate frequency band.

In addition, rs-fcMRI data can be used to define a tACS target map much as discussed above. Although fMRI is capable of capturing relatively slow metabolic changes, it has been shown to correlate with local field potentials (LFPs) in the gamma range, and anti-correlate at slow frequencies (Mukamel et al. (2005)). It would follow that there are two possible scenarios. For tACS frequencies in the low frequency range (<25 Hz), fMRI and LFP (and presumably, EEG) data anti-correlate, hence tACS would be inhibitory with respect to the target map. In the high frequency range (25-300 Hz), tACS would be expected to act in an excitatory fashion. DC stimulation could be combined to target the complementary effect achieved by the chosen tACS frequency. E.g., for high frequency tACS, optimization could be defined by stimulation at the appropriate tACS frequency at the excitatory target map sites, with DC inhibitory stimulation at the complementary sites.

The next order of complexity will involve stimulation at different sites with different frequencies. From the optimization point of view it would suffice to provide target maps for each frequency—the generalization of the least-squares approach described below would be immediate by the principle of superposition (this time in the frequency domain)—with the error function generalized as a weighted sum of error functions for each frequency component.

Going one step further, recent results using natural or even "endogenous" stimulation waveforms in vitro (which could be derived from personalized EEG in humans) are particularly intriguing (Fröhlich and McCormick (2010)). While tCS technology allows for all these possibilities, research protocols need to be defined on solid neurophysiological hypotheses, given the large parameter space (which includes the number of electrodes, locations, current intensities and current waveforms at each electrode).

A person skilled in the art could introduce changes and modifications in the embodiments described without departing from the scope of the invention as it is defined in the attached claims.

The invention claimed is:

1. A method for optimizing the configuration of multisite transcranial current stimulation, comprising:
providing an electric field characteristic target map on for a brain's cortex, said target map including multiple cortical targets and desired values for the electrical field at each of the multiple cortical targets to modulate neuronal function, where said multiple cortical targets are localized and/or continuously varying and spatially extended;
providing a weight map for the cortical surface specifying a degree of relative importance for each of the multiple cortical targets for the purposes of optimization;
calculating, based on said target and weight maps, optimal currents and optimal number and locations for a plurality of electrodes intended for providing transcranial current stimulation to globally stimulate at once said multiple cortical targets, wherein the calculating is performed under constraints regarding at least maximal electrode number and maximal current at each electrode and the total current injected into the brain by all electrodes at any time; and
delivering the transcranial current stimulation to a subject to simultaneously globally stimulate the multiple cortical targets in the target map with excitatory, inhibitory or neutral stimulation, using the determined number of electrodes, the determined optimal currents, and the determined optimal locations.

2. The method of claim 1, wherein said multiple cortical targets are final targets.

3. The method of claim 1, wherein said multiple cortical targets are intermediary targets having spatially extended patterns that indirectly affect, via neuronal interaction, cortical or deeper targets in the brain.

4. The method of claim 3, comprising performing said calculation of optimal currents and electrode locations based on said spatially extended patterns and to their positive or negative correlation with a deep brain stimulation target.

5. The method of claim 1, wherein said spatially extended patterns are specific to a pathology and/or to a patient.

6. The method of claim 1, wherein said target map is obtained from brain activity data obtained by means of a brain monitoring technology.

7. The method of claim 6, wherein said brain monitoring technology is at least one of fMRI, rs-fcMRI, PET, EEG and MEG, or a combination thereof.

8. The method of claim 1, wherein said calculation of optimal currents and optimal electrode locations is performed based on an optimization of several electric field components, including electric field distribution and orientation.

9. The method of claim 8, wherein said target map includes the definition of the multiple cortical targets based on a coordinate system relative to the cortical surface, with the multiple cortical targets including targets for at least normal components of respective electric field vectors.

10. The method of claim 9, wherein said target map further includes targets for tangential components of respective electric field vectors.

11. The method of claim 8, comprising using a realistic head model and electric field modeling to perform said optimization of several electric field components, where said electric field distribution and orientation is relative to the grey matter and white matter surfaces.

12. The method of claim 1, wherein in order to increase focality for a cortical target, said calculation generates zero or near zero electric field values for those electrodes surrounding said cortical target of increased focality.

13. The method of claim 1, wherein said maximum number of electrodes is eight.

14. The method of claim 13, wherein said plurality of electrodes are arranged according to an EEG 10-20 or 10-10 montage scheme with determined electrode positions.

15. The method of claim 11, comprising using constrained least squares to optimize current intensities and a genetic algorithm to optimize electrode number and locations.

16. The method of claim 11, wherein said realistic head model is a multilayer finite element model of a realistic head, generic or specific to a patient.

17. The method of claim 1, wherein said transcranial stimulation is at least one or a combination of transcranial direct current stimulation, transcranial alternating current stimulation, transcranial random noise stimulation or stimulation with a more generic current waveform.

18. The method of claim 1, wherein said provision of said target and weight maps and said calculation of optimal currents and optimal electrodes locations are performed automatically.

19. A system for optimizing the configuration of multisite transcranial current stimulation, comprising at least one processor for:
   providing a target map for the brain's cortex, said target map including multiple cortical targets and desired values for the electrical field at each of the multiple cortical targets to modulate neuronal function, where said multiple cortical targets are localized and/or continuously varying and spatially extended; and
   providing a weight map for the cortical surface specifying a degree of relative importance for each of the multiple cortical targets for the purposes of optimization;
   calculating, based on said target and weight maps, optimal currents and optimal number and locations for a plurality of electrodes intended for providing transcranial current stimulation to globally stimulate at once said multiple cortical targets, wherein the calculating is performed under constraints regarding at least maximal electrode number and maximal current at each electrode and the total current injected into the brain by all electrodes at any time; and
   delivering the transcranial current stimulation to a subject to simultaneously globally stimulate the multiple cortical targets in the target map with excitatory, inhibitory or neutral stimulation, using the determined number of electrodes, the determined optimal currents, and the determined optimal locations.

20. A computer-readable medium containing program instructions for a computer to perform a method for optimizing the configuration of multisite transcranial current stimulation comprising:
   providing a target map for the brain's cortex, said target map including multiple cortical targets and desired values for the electrical field at each of the multiple cortical targets to modulate neuronal function, where said multiple cortical targets are localized and/or continuously varying and spatially extended;
   providing a weight map for the cortical surface specifying a degree of relative importance for each of the multiple cortical targets for the purposes of optimization;
   calculating, based on said target and weight maps, optimal currents and optimal number and locations for a plurality of electrodes intended for providing transcranial current stimulation to globally stimulate at once said multiple cortical targets, wherein the calculating is performed under constraints regarding at least maximal electrode number and maximal current at each electrode and the total current injected into the brain by all electrodes at any time; and
   controlling delivery of the transcranial current stimulation to a subject to simultaneously globally stimulate the multiple cortical targets in the target map with excitatory, inhibitory or neutral stimulation, using the determined number of electrodes, the determined optimal currents, and the determined optimal locations.

* * * * *